(12) United States Patent
Soo

(10) Patent No.: US 9,358,122 B2
(45) Date of Patent: Jun. 7, 2016

(54) INTERBODY SPACER

(75) Inventor: Teck Soo, Franklin, MI (US)

(73) Assignee: K2M, Inc., Leesburg, VA (US)

( * ) Notice: Subject to any disclaimer, the term of this patent is extended or adjusted under 35 U.S.C. 154(b) by 68 days.

(21) Appl. No.: 13/346,179

(22) Filed: Jan. 9, 2012

(65) Prior Publication Data

US 2012/0179261 A1 Jul. 12, 2012

Related U.S. Application Data

(60) Provisional application No. 61/430,558, filed on Jan. 7, 2011.

(51) Int. Cl.
*A61F 2/44* (2006.01)
*A61F 2/46* (2006.01)
*A61F 2/30* (2006.01)
*A61F 2/28* (2006.01)

(52) U.S. Cl.
CPC .............. *A61F 2/4455* (2013.01); *A61F 2/4611* (2013.01); *A61F 2/4465* (2013.01); *A61F 2002/2835* (2013.01); *A61F 2002/3008* (2013.01); *A61F 2002/3079* (2013.01); *A61F 2002/3093* (2013.01); *A61F 2002/30131* (2013.01); *A61F 2002/30785* (2013.01); *A61F 2002/30789* (2013.01); *A61F 2002/30892* (2013.01); *A61F 2002/30904* (2013.01); *A61F 2002/4475* (2013.01); *A61F 2310/00017* (2013.01); *A61F 2310/00023* (2013.01); *A61F 2310/00029* (2013.01); *A61F 2310/00359* (2013.01)

(58) Field of Classification Search
CPC ............ A61F 2002/30622; A61F 2002/30367; A61F 2002/30372; A61F 2/30767; A61F 2002/30403; A61F 2002/30836; A61F 2002/30843; A61F 2002/30881; A61F 2002/30891; A61F 2002/30899; A61F 2002/3092

USPC ............. 606/246–249, 286; 623/17.11–17.16
See application file for complete search history.

(56) References Cited

U.S. PATENT DOCUMENTS 3,741,205 A 6/1973 Markolf et al.
4,599,086 A 7/1986 Doty
(Continued)

FOREIGN PATENT DOCUMENTS

EP 0 664 994 8/1995
EP 1 415 623 5/2004
(Continued)

OTHER PUBLICATIONS

US 7,520,878, 4/2009, Michelson (withdrawn).

*Primary Examiner* — Mary Hoffman
*Assistant Examiner* — Tara R Carter
(74) *Attorney, Agent, or Firm* — Carter, DeLuca, Farrell & Schmidt, LLP

(57) ABSTRACT

An interbody spacer includes a connecting portion and a pair of leg portions extending from the connecting portion. The connecting portion and the pair of leg portions define top and bottom surfaces configured and adapted to engage first and second vertebral bodies, respectively, and inner and outer sidewalls extending between the top and bottom surfaces. In particular, the top and bottom surfaces of the leg portions include first projections defining a first angle with the respective top and bottom surfaces of the leg portions. The top and bottom surfaces of the connecting portion include second projections defining a second angle with the respective top and bottom surfaces of the connecting portion. The first and second angles are different.

18 Claims, 8 Drawing Sheets

(56) References Cited

U.S. PATENT DOCUMENTS

| | | | |
|---|---|---|---|
| 4,834,757 A * | | 5/1989 | Brantigan .................. 623/17.11 |
| 4,860,746 A | | 8/1989 | Yoon |
| 4,904,261 A | | 2/1990 | Dove et al. |
| 5,015,247 A | | 5/1991 | Michelson |
| 5,053,036 A | | 10/1991 | Perren et al. |
| 5,055,104 A | | 10/1991 | Ray |
| 5,180,381 A | | 1/1993 | Aust et al. |
| 5,192,327 A | | 3/1993 | Brantigan |
| 5,290,312 A | | 3/1994 | Kojimoto et al. |
| 5,306,307 A | | 4/1994 | Senter et al. |
| 5,425,772 A | | 6/1995 | Brantigan |
| 5,431,658 A | | 7/1995 | Moskovich |
| 5,443,514 A | | 8/1995 | Steffee |
| 5,458,638 A | | 10/1995 | Kuslich et al. |
| 5,489,307 A | | 2/1996 | Kuslich et al. |
| 5,520,690 A | | 5/1996 | Errico et al. |
| 5,554,191 A | | 9/1996 | Lahille et al. |
| 5,571,192 A | | 11/1996 | Schönhöffer |
| 5,599,279 A | | 2/1997 | Slotman et al. |
| 5,609,635 A | | 3/1997 | Michelson |
| 5,645,596 A | | 7/1997 | Kim et al. |
| 5,766,252 A | | 6/1998 | Henry et al. |
| 5,776,198 A | | 7/1998 | Rabbe et al. |
| 5,800,433 A | | 9/1998 | Benzel et al. |
| 5,843,082 A | | 12/1998 | Yuan et al. |
| 5,860,973 A | | 1/1999 | Michelson |
| 5,868,746 A | | 2/1999 | Sarver et al. |
| 5,888,222 A | | 3/1999 | Coates et al. |
| 5,904,683 A | | 5/1999 | Pohndorf et al. |
| 5,968,098 A | | 10/1999 | Winslow |
| 5,989,290 A | | 11/1999 | Biedermann et al. |
| 6,045,579 A | | 4/2000 | Hochshuler et al. |
| 6,099,531 A | | 8/2000 | Bonutti |
| 6,143,032 A | | 11/2000 | Schafer et al. |
| 6,152,927 A | | 11/2000 | Farris et al. |
| 6,200,348 B1 | | 3/2001 | Biedermann et al. |
| 6,241,770 B1 | | 6/2001 | Michelson |
| 6,241,771 B1 | | 6/2001 | Gresser et al. |
| 6,245,108 B1 | | 6/2001 | Biscup |
| 6,296,665 B1 | | 10/2001 | Strnad et al. |
| 6,322,562 B1 | | 11/2001 | Wolter |
| 6,325,827 B1 | | 12/2001 | Lin |
| 6,342,074 B1 | | 1/2002 | Simpson |
| 6,350,283 B1 | | 2/2002 | Michelson |
| 6,364,880 B1 | | 4/2002 | Michelson |
| 6,395,034 B1 | | 5/2002 | Suddaby |
| 6,423,063 B1 | | 7/2002 | Bonutti |
| 6,447,544 B1 | | 9/2002 | Michelson |
| 6,447,547 B1 | | 9/2002 | Michelson |
| 6,478,823 B1 | | 11/2002 | Michelson |
| 6,482,233 B1 | | 11/2002 | Aebi et al. |
| 6,520,996 B1 | | 2/2003 | Manasas et al. |
| 6,558,423 B1 | | 5/2003 | Michelson |
| 6,569,168 B2 | | 5/2003 | Lin |
| 6,610,089 B1 | | 8/2003 | Liu et al. |
| 6,610,090 B1 | | 8/2003 | Böhm |
| 6,629,998 B1 | | 10/2003 | Lin |
| 6,635,086 B2 * | | 10/2003 | Lin ............................ 623/17.11 |
| 6,676,703 B2 | | 1/2004 | Biscup |
| 6,716,214 B1 | | 4/2004 | Jackson |
| 6,719,794 B2 | | 4/2004 | Gerber et al. |
| 6,740,117 B2 | | 5/2004 | Ralph |
| 6,743,255 B2 | | 6/2004 | Ferree |
| 6,746,484 B1 | | 6/2004 | Liu et al. |
| 6,770,074 B2 | | 8/2004 | Michelson |
| 6,808,538 B2 | | 10/2004 | Paponneau |
| 6,827,740 B1 | | 12/2004 | Michelson |
| 6,890,355 B2 | | 5/2005 | Michelson |
| 6,942,698 B1 | | 9/2005 | Jackson |
| 6,964,687 B1 * | | 11/2005 | Bernard et al. ............. 623/17.16 |
| 6,972,019 B2 | | 12/2005 | Michelson |
| 6,984,234 B2 | | 1/2006 | Bray |
| 6,986,772 B2 | | 1/2006 | Michelson |
| 6,991,654 B2 | | 1/2006 | Foley |
| 7,001,385 B2 | | 2/2006 | Bonutti |
| 7,033,394 B2 | | 4/2006 | Michelson |
| 7,041,135 B2 | | 5/2006 | Michelson |
| 7,052,499 B2 | | 5/2006 | Steger et al. |
| 7,070,598 B2 | | 7/2006 | Lim et al. |
| 7,077,864 B2 | | 7/2006 | Byrd, III et al. |
| 7,087,055 B2 | | 8/2006 | Lim et al. |
| 7,137,997 B2 | | 11/2006 | Paul |
| 7,175,624 B2 | | 2/2007 | Konieczynski et al. |
| 7,195,643 B2 | | 3/2007 | Jackson |
| 7,229,443 B2 | | 6/2007 | Eberlein et al. |
| 7,229,477 B2 | | 6/2007 | Biscup |
| 7,276,081 B1 | | 10/2007 | Coates et al. |
| 7,285,134 B2 | | 10/2007 | Berry et al. |
| 7,311,734 B2 | | 12/2007 | Van Hoeck et al. |
| 7,318,825 B2 | | 1/2008 | Butler et al. |
| 7,341,587 B2 | | 3/2008 | Molz, IV et al. |
| 7,341,590 B2 | | 3/2008 | Ferree |
| 7,341,600 B2 | | 3/2008 | Lange et al. |
| 7,341,601 B2 | | 3/2008 | Eisermann et al. |
| 7,344,537 B1 | | 3/2008 | Mueller |
| 7,344,539 B2 | | 3/2008 | Serhan et al. |
| 7,344,564 B2 | | 3/2008 | Sweeney |
| 7,347,873 B2 | | 3/2008 | Paul et al. |
| RE40,260 E | | 4/2008 | Bühler |
| 7,351,261 B2 | | 4/2008 | Casey |
| 7,351,262 B2 | | 4/2008 | Bindseil et al. |
| 7,354,442 B2 | | 4/2008 | Sasso et al. |
| 7,354,452 B2 | | 4/2008 | Foley |
| 7,354,453 B2 | | 4/2008 | McAfee |
| 7,361,192 B2 | | 4/2008 | Doty |
| 7,361,193 B2 | | 4/2008 | Frey et al. |
| 7,364,589 B2 | | 4/2008 | Eisermann |
| 7,367,978 B2 | | 5/2008 | Drewry et al. |
| 7,371,238 B2 | | 5/2008 | Soboleski et al. |
| 7,371,239 B2 | | 5/2008 | Dec et al. |
| 7,371,408 B1 | | 5/2008 | Petersen et al. |
| 7,371,409 B2 | | 5/2008 | Petersen et al. |
| 7,371,410 B2 | | 5/2008 | Petersen |
| 7,374,577 B2 | | 5/2008 | Kim et al. |
| 7,377,921 B2 | | 5/2008 | Studer et al. |
| 7,377,922 B2 | | 5/2008 | Barker |
| 7,377,923 B2 | | 5/2008 | Purcell et al. |
| 7,377,934 B2 | | 5/2008 | Lin et al. |
| 7,377,942 B2 | | 5/2008 | Berry |
| 7,378,144 B2 | | 5/2008 | DeMeo et al. |
| 7,381,178 B2 | | 6/2008 | Winkler et al. |
| 7,381,223 B2 | | 6/2008 | Kovacevic |
| 7,381,752 B2 | | 6/2008 | Muratoglu |
| 7,383,164 B2 | | 6/2008 | Aram et al. |
| 7,384,431 B2 | | 6/2008 | Berry |
| 7,387,643 B2 | | 6/2008 | Michelson |
| 7,393,361 B2 | | 7/2008 | Zubok et al. |
| 7,396,365 B2 | | 7/2008 | Michelson |
| 7,402,176 B2 | | 7/2008 | Malek |
| 7,404,818 B2 | | 7/2008 | Miller et al. |
| 7,407,513 B2 | | 8/2008 | Alleyne et al. |
| 7,409,070 B2 | | 8/2008 | Pitulia |
| 7,410,501 B2 | | 8/2008 | Michelson |
| 7,416,553 B2 | | 8/2008 | Patel et al. |
| 7,419,505 B2 | | 9/2008 | Fleischmann et al. |
| 7,419,506 B2 | | 9/2008 | Hestad et al. |
| 7,419,714 B1 | | 9/2008 | Magerl et al. |
| 7,422,597 B1 | | 9/2008 | Alby |
| 7,427,292 B2 | | 9/2008 | Sachs |
| 7,427,293 B2 | | 9/2008 | Nycz et al. |
| 7,427,294 B2 | | 9/2008 | Thramann et al. |
| 7,427,295 B2 | | 9/2008 | Ellman et al. |
| 7,429,270 B2 | | 9/2008 | Baumgartner et al. |
| 7,431,722 B1 | | 10/2008 | Michelson |
| 7,431,734 B2 | | 10/2008 | Danoff et al. |
| 7,431,735 B2 | | 10/2008 | Liu et al. |
| 7,435,260 B2 | | 10/2008 | Ferree |
| 7,435,261 B1 | | 10/2008 | Castro |
| 7,435,262 B2 | | 10/2008 | Michelson |
| 7,435,372 B2 | | 10/2008 | Mimnaugh et al. |
| 7,442,208 B2 | | 10/2008 | Mathieu et al. |
| 7,442,209 B2 | | 10/2008 | Michelson |
| 7,442,210 B2 | | 10/2008 | Segal et al. |
| 7,442,211 B2 | | 10/2008 | de Villiers et al. |

(56) References Cited

U.S. PATENT DOCUMENTS

| | | |
|---|---|---|
| 7,445,633 B2 | 11/2008 | Hoerger et al. |
| 7,445,634 B2 | 11/2008 | Trieu |
| 7,445,635 B2 | 11/2008 | Fallin et al. |
| 7,445,636 B2 | 11/2008 | Michelson |
| 7,445,637 B2 | 11/2008 | Taylor |
| 7,452,359 B1 | 11/2008 | Michelson |
| 7,452,379 B2 | 11/2008 | Mitchell |
| 7,455,672 B2 | 11/2008 | Michelson |
| 7,455,683 B2 | 11/2008 | Geissler et al. |
| 7,455,684 B2 | 11/2008 | Gradel et al. |
| 7,455,685 B2 | 11/2008 | Justis |
| 7,455,692 B2 | 11/2008 | Michelson |
| 7,458,975 B2 | 12/2008 | May et al. |
| 7,462,195 B1 | 12/2008 | Michelson |
| 7,462,196 B2 | 12/2008 | Fraser et al. |
| 7,465,305 B2 | 12/2008 | Liu et al. |
| 7,465,317 B2 | 12/2008 | Malberg et al. |
| 7,468,075 B2 | 12/2008 | Lang et al. |
| 7,468,076 B2 | 12/2008 | Zubok et al. |
| 7,470,273 B2 | 12/2008 | Dougherty-Shah |
| 7,473,256 B2 | 1/2009 | Assell et al. |
| 7,473,276 B2 | 1/2009 | Aebi et al. |
| 7,473,277 B2 | 1/2009 | Boyer, II et al. |
| 7,476,251 B2 | 1/2009 | Zucherman et al. |
| 7,476,252 B2 | 1/2009 | Foley |
| 7,479,160 B2 | 1/2009 | Branch et al. |
| 7,479,530 B2 | 1/2009 | Hughes et al. |
| 7,481,812 B2 | 1/2009 | Frey et al. |
| 7,481,831 B2 | 1/2009 | Bonutti |
| 7,481,839 B2 | 1/2009 | Zucherman et al. |
| 7,481,840 B2 | 1/2009 | Zucherman et al. |
| 7,485,120 B2 | 2/2009 | Ray |
| 7,485,132 B1 | 2/2009 | McBride et al. |
| 7,485,133 B2 | 2/2009 | Cannon et al. |
| 7,485,134 B2 | 2/2009 | Simonson |
| 7,485,145 B2 | 2/2009 | Purcell |
| 7,485,146 B1 | 2/2009 | Crook et al. |
| 7,485,147 B2 | 2/2009 | Pappas et al. |
| 7,488,330 B2 | 2/2009 | Stad |
| 7,491,180 B2 | 2/2009 | Pacheco |
| 7,491,205 B1 | 2/2009 | Michelson |
| 7,491,218 B2 | 2/2009 | Landry et al. |
| 7,491,236 B2 | 2/2009 | Cragg et al. |
| 7,491,237 B2 | 2/2009 | Randall et al. |
| 7,491,240 B1 | 2/2009 | Carver et al. |
| 7,491,241 B2 | 2/2009 | Errico et al. |
| 7,494,507 B2 | 2/2009 | Dixon et al. |
| 7,494,508 B2 | 2/2009 | Zeegers |
| 7,494,664 B2 | 2/2009 | Sotome et al. |
| 7,497,876 B2 | 3/2009 | Tuke et al. |
| 7,500,978 B2 | 3/2009 | Gorensek et al. |
| 7,500,991 B2 | 3/2009 | Bartish, Jr. et al. |
| 7,500,992 B2 | 3/2009 | Li |
| 7,503,918 B2 | 3/2009 | Baccelli et al. |
| 7,503,933 B2 | 3/2009 | Michelson |
| 7,503,934 B2 | 3/2009 | Eisermann et al. |
| 7,503,935 B2 | 3/2009 | Zucherman et al. |
| 7,503,936 B2 | 3/2009 | Trieu |
| 7,507,241 B2 | 3/2009 | Levy et al. |
| 7,507,253 B2 | 3/2009 | Nordquist |
| 7,507,254 B2 | 3/2009 | Yim et al. |
| 7,507,255 B2 | 3/2009 | Ralph et al. |
| 7,513,911 B2 | 4/2009 | Lambrecht et al. |
| 7,517,358 B2 | 4/2009 | Petersen |
| 7,517,363 B2 | 4/2009 | Rogers et al. |
| 7,517,539 B1 | 4/2009 | Lee et al. |
| 7,520,880 B2 | 4/2009 | Claypool et al. |
| 7,520,887 B2 | 4/2009 | Maxy et al. |
| 7,520,900 B2 | 4/2009 | Trieu |
| 7,524,323 B2 | 4/2009 | Malandain |
| 7,524,324 B2 | 4/2009 | Winslow et al. |
| 7,524,333 B2 | 4/2009 | Lambrecht et al. |
| 7,524,335 B2 | 4/2009 | Slivka et al. |
| 7,527,611 B2 | 5/2009 | Sweeney |
| 7,527,640 B2 | 5/2009 | Ziolo et al. |
| 7,527,649 B1 | 5/2009 | Blain |
| 7,530,810 B2 | 5/2009 | Clement |
| 7,531,001 B2 | 5/2009 | De Villiers et al. |
| 7,531,002 B2 | 5/2009 | Sutton et al. |
| 7,534,254 B1 | 5/2009 | Michelson |
| 7,534,264 B2 | 5/2009 | Fischer |
| 7,534,265 B1 | 5/2009 | Boyd et al. |
| 7,534,266 B2 | 5/2009 | Kluer |
| 7,534,267 B2 | 5/2009 | Eckman |
| 7,534,268 B2 | 5/2009 | Hudgins et al. |
| 7,534,451 B2 | 5/2009 | Erbe et al. |
| 7,537,611 B2 | 5/2009 | Lee |
| 7,537,612 B2 | 5/2009 | Kunzler |
| 7,537,613 B2 | 5/2009 | Arnin et al. |
| 7,537,614 B2 | 5/2009 | Baumgartner et al. |
| 7,537,615 B2 | 5/2009 | Lemaire |
| 7,537,616 B1 | 5/2009 | Branch et al. |
| 7,537,617 B2 | 5/2009 | Bindsell et al. |
| 7,537,782 B2 | 5/2009 | Calhoun et al. |
| 7,540,882 B2 | 6/2009 | Michelson |
| 7,544,208 B1 | 6/2009 | Mueller et al. |
| 7,547,319 B2 | 6/2009 | Segal et al. |
| 7,547,324 B2 | 6/2009 | Cragg et al. |
| 7,547,325 B2 | 6/2009 | Biedermann et al. |
| 7,547,326 B2 | 6/2009 | Bhatnagar et al. |
| 7,549,993 B2 | 6/2009 | McCombe et al. |
| 7,549,999 B2 | 6/2009 | Zucherman et al. |
| 7,550,008 B2 | 6/2009 | Ralph et al. |
| 7,550,009 B2 | 6/2009 | Arnin et al. |
| 7,550,010 B2 | 6/2009 | Humphreys et al. |
| 7,550,011 B2 | 6/2009 | McKay et al. |
| 7,553,313 B2 | 6/2009 | Bagby |
| 7,553,320 B2 | 6/2009 | Molz, IV et al. |
| 7,553,329 B2 | 6/2009 | Lambrecht et al. |
| 7,553,330 B2 | 6/2009 | Lambrecht et al. |
| 7,553,539 B2 | 6/2009 | Bruce et al. |
| 7,556,500 B2 | 7/2009 | Ihde |
| 7,556,648 B2 | 7/2009 | Picha et al. |
| 7,556,649 B2 | 7/2009 | Moehlenbruck et al. |
| 7,556,650 B2 | 7/2009 | Collins et al. |
| 7,556,651 B2 | 7/2009 | Humphreys et al. |
| 7,559,932 B2 | 7/2009 | Truckai et al. |
| 7,563,264 B2 | 7/2009 | Landry et al. |
| 7,563,274 B2 | 7/2009 | Justis et al. |
| 7,563,281 B2 | 7/2009 | Sears et al. |
| 7,563,282 B2 | 7/2009 | Lambrecht et al. |
| 7,563,283 B2 | 7/2009 | Kwak |
| 7,563,285 B2 | 7/2009 | Ralph et al. |
| 7,563,286 B2 | 7/2009 | Gerber et al. |
| 7,563,455 B2 | 7/2009 | McKay |
| 7,566,345 B1 | 7/2009 | Fallin et al. |
| 7,566,346 B2 | 7/2009 | Kirschman |
| 7,569,054 B2 | 8/2009 | Michelson |
| 7,569,056 B2 | 8/2009 | Cragg et al. |
| 7,569,068 B2 | 8/2009 | Ramare |
| 7,569,074 B2 | 8/2009 | Eisermann et al. |
| 7,569,285 B2 | 8/2009 | Schwartz et al. |
| 7,569,620 B2 | 8/2009 | Muratoglu et al. |
| 7,572,276 B2 | 8/2009 | Lim et al. |
| 7,572,281 B2 | 8/2009 | Runco et al. |
| 7,572,291 B2 | 8/2009 | Gil et al. |
| 7,575,580 B2 | 8/2009 | Lim et al. |
| 7,575,588 B2 | 8/2009 | Barker et al. |
| 7,575,598 B2 | 8/2009 | Albert et al. |
| 7,575,599 B2 | 8/2009 | Villiers et al. |
| 7,575,600 B2 | 8/2009 | Zucherman et al. |
| 7,575,601 B2 | 8/2009 | Dickson |
| 7,578,833 B2 | 8/2009 | Bray |
| 7,578,834 B2 | 8/2009 | Abdou |
| 7,578,844 B2 | 8/2009 | Sklar et al. |
| 7,578,845 B2 | 8/2009 | Nies et al. |
| 7,578,847 B2 | 8/2009 | Albert et al. |
| 7,578,848 B2 | 8/2009 | Albert et al. |
| 7,578,849 B2 | 8/2009 | Trieu |
| 7,582,114 B2 | 9/2009 | Albert et al. |
| 7,582,309 B2 | 9/2009 | Rosenberg et al. |
| 7,585,299 B2 | 9/2009 | Rezach |
| 7,585,312 B2 | 9/2009 | Rawlins et al. |
| 7,585,323 B2 | 9/2009 | Masini et al. |

(56) References Cited

U.S. PATENT DOCUMENTS

| | | |
|---|---|---|
| 7,585,324 B2 | 9/2009 | Albert et al. |
| 7,585,325 B2 | 9/2009 | Schneid et al. |
| 7,585,326 B2 | 9/2009 | de Villiers et al. |
| 7,588,588 B2 | 9/2009 | Spitler et al. |
| 7,588,589 B2 | 9/2009 | Falahee |
| 7,588,591 B2 | 9/2009 | Hartmann et al. |
| 7,588,599 B2 | 9/2009 | Sweeney |
| 7,588,600 B2 | 9/2009 | Benzel et al. |
| 7,588,601 B2 | 9/2009 | Le Couedic et al. |
| 7,588,603 B2 | 9/2009 | Leonard |
| 7,591,822 B2 | 9/2009 | Olson, Jr. et al. |
| 7,591,836 B2 | 9/2009 | Dick et al. |
| 7,591,837 B2 | 9/2009 | Goldsmith |
| 7,591,851 B2 | 9/2009 | Winslow et al. |
| 7,591,852 B2 | 9/2009 | Prosser |
| 7,591,853 B2 | 9/2009 | Felt et al. |
| 7,594,931 B2 | 9/2009 | Louis et al. |
| 7,594,932 B2 | 9/2009 | Aferzon et al. |
| 7,597,712 B2 | 10/2009 | Parenteau et al. |
| 7,597,713 B2 | 10/2009 | Baumgartner et al. |
| 7,597,714 B2 | 10/2009 | Suddaby |
| 7,601,170 B2 | 10/2009 | Winslow et al. |
| 7,601,171 B2 | 10/2009 | Ainsworth et al. |
| 7,601,172 B2 | 10/2009 | Segal et al. |
| 7,601,173 B2 | 10/2009 | Messerli et al. |
| 7,601,174 B2 | 10/2009 | Kelly et al. |
| 7,603,192 B2 | 10/2009 | Martin et al. |
| 7,604,664 B2 | 10/2009 | Ralph et al. |
| 7,608,095 B2 | 10/2009 | Yuan et al. |
| 7,608,104 B2 | 10/2009 | Yuan et al. |
| 7,608,105 B2 | 10/2009 | Pavlov et al. |
| 7,608,106 B2 | 10/2009 | Reiley |
| 7,608,107 B2 | 10/2009 | Michelson |
| 7,608,108 B2 | 10/2009 | Bhatnagar et al. |
| 7,611,518 B2 | 11/2009 | Walder et al. |
| 7,611,536 B2 | 11/2009 | Michelson |
| 7,611,537 B2 | 11/2009 | Carls et al. |
| 7,611,538 B2 | 11/2009 | Belliard et al. |
| 7,615,052 B2 | 11/2009 | Serbousek |
| 7,615,076 B2 | 11/2009 | Cauthen, III et al. |
| 7,615,077 B2 | 11/2009 | Melkent et al. |
| 7,615,078 B2 | 11/2009 | White et al. |
| 7,615,079 B2 | 11/2009 | Flickinger et al. |
| 7,618,418 B2 | 11/2009 | Malandain |
| 7,618,439 B2 | 11/2009 | Zubok et al. |
| 7,618,440 B2 | 11/2009 | Gray et al. |
| 7,618,453 B2 | 11/2009 | Goble et al. |
| 7,618,454 B2 | 11/2009 | Bentley et al. |
| 7,618,455 B2 | 11/2009 | Goble et al. |
| 7,618,456 B2 | 11/2009 | Mathieu et al. |
| 7,618,458 B2 | 11/2009 | Biedermann et al. |
| 7,618,459 B2 | 11/2009 | Justin et al. |
| 7,618,460 B2 | 11/2009 | Boyd |
| 7,618,461 B2 | 11/2009 | Trieu |
| 7,621,912 B2 | 11/2009 | Harms et al. |
| 7,621,938 B2 | 11/2009 | Molz, IV |
| 7,621,950 B1 | 11/2009 | Globerman et al. |
| 7,621,951 B2 | 11/2009 | Glenn et al. |
| 7,621,952 B2 | 11/2009 | Truckai et al. |
| 7,621,953 B2 | 11/2009 | Braddock, Jr. et al. |
| 7,621,954 B2 | 11/2009 | Yuksel et al. |
| 7,621,955 B2 | 11/2009 | Globe et al. |
| 7,621,956 B2 | 11/2009 | Paul et al. |
| 7,621,957 B2 | 11/2009 | Errico et al. |
| 7,621,958 B2 | 11/2009 | Zdeblick et al. |
| 7,621,959 B2 | 11/2009 | Yuksel et al. |
| 7,621,960 B2 | 11/2009 | Boyd et al. |
| 7,621,963 B2 | 11/2009 | Simon et al. |
| 7,625,377 B2 | 12/2009 | Veldhuizen et al. |
| 7,625,379 B2 | 12/2009 | Puno et al. |
| 7,625,394 B2 | 12/2009 | Molz, IV et al. |
| 7,628,813 B2 | 12/2009 | Link |
| 7,628,814 B2 | 12/2009 | Studer et al. |
| 7,628,815 B2 | 12/2009 | Baumgartner et al. |
| 7,628,816 B2 | 12/2009 | Mageri et al. |
| 7,632,278 B2 | 12/2009 | Jansen et al. |
| 7,632,294 B2 | 12/2009 | Milbodker et al. |
| 7,632,311 B2 | 12/2009 | Seedhom et al. |
| 7,632,312 B2 | 12/2009 | Leclercq |
| 7,632,313 B2 | 12/2009 | Bhatnagar et al. |
| 7,635,368 B2 | 12/2009 | Errico et al. |
| 7,635,371 B2 | 12/2009 | McGahan et al. |
| 7,635,378 B2 | 12/2009 | Zucherman et al. |
| 7,635,389 B2 | 12/2009 | Yu et al. |
| 7,636,459 B2 | 12/2009 | Dore et al. |
| 7,637,950 B2 | 12/2009 | Baccelli et al. |
| 7,637,951 B2 | 12/2009 | Michelson |
| 7,637,952 B2 | 12/2009 | Landry et al. |
| 7,637,953 B2 | 12/2009 | Branch et al. |
| 7,637,954 B2 | 12/2009 | Michelson |
| 7,637,955 B2 | 12/2009 | Marik et al. |
| 7,637,956 B2 | 12/2009 | Lechmann et al. |
| 7,641,677 B2 | 1/2010 | Weiner et al. |
| 7,641,690 B2 | 1/2010 | Abdou |
| 7,641,692 B2 | 1/2010 | Bryan et al. |
| 7,641,693 B2 | 1/2010 | Gutlin et al. |
| 7,645,281 B2 | 1/2010 | Marik |
| 7,645,282 B2 | 1/2010 | Huxel et al. |
| 7,645,294 B2 | 1/2010 | Kalfas et al. |
| 7,645,295 B2 | 1/2010 | Osman |
| 7,645,301 B2 | 1/2010 | Hudgins et al. |
| 7,648,520 B2 | 1/2010 | Markworth |
| 7,648,521 B2 | 1/2010 | Hestad |
| 7,648,529 B2 | 1/2010 | An et al. |
| 7,648,735 B2 | 1/2010 | Hunter et al. |
| 7,651,495 B2 | 1/2010 | McDevitt et al. |
| 7,651,496 B2 | 1/2010 | Keegan et al. |
| 7,651,516 B2 | 1/2010 | Petit et al. |
| 7,651,517 B2 | 1/2010 | Konieczynski et al. |
| 7,655,008 B2 | 2/2010 | Lenke et al. |
| 7,655,012 B2 | 2/2010 | DiPoto et al. |
| 7,655,025 B2 | 2/2010 | Ritland |
| 7,655,026 B2 | 2/2010 | Justis et al. |
| 7,655,027 B2 | 2/2010 | Michelson |
| 7,655,028 B2 | 2/2010 | Kirschman |
| 7,655,042 B2 | 2/2010 | Foley et al. |
| 7,655,043 B2 | 2/2010 | Peterman et al. |
| 7,655,045 B2 | 2/2010 | Richelsoph |
| 7,655,046 B2 | 2/2010 | Dryer et al. |
| 7,655,615 B2 | 2/2010 | Baumgartner |
| 7,658,739 B2 | 2/2010 | Shluzas |
| 7,658,754 B2 | 2/2010 | Zhang et al. |
| 7,658,765 B2 | 2/2010 | Lambrecht et al. |
| 7,658,766 B2 | 2/2010 | Melkent et al. |
| 7,658,768 B2 | 2/2010 | Miller et al. |
| 7,661,164 B2 | 2/2010 | Chen |
| 7,662,182 B2 | 2/2010 | Zubok et al. |
| 7,662,183 B2 | 2/2010 | Haines |
| 7,662,184 B2 | 2/2010 | Edwards et al. |
| 7,662,185 B2 | 2/2010 | Alfaro et al. |
| 7,662,186 B2 | 2/2010 | Bagga et al. |
| 7,662,187 B2 | 2/2010 | Zucherman et al. |
| 7,666,207 B2 | 2/2010 | Schlapfer et al. |
| 7,666,209 B2 | 2/2010 | Zucherman et al. |
| 7,666,211 B2 | 2/2010 | Perez-Cruet et al. |
| 7,666,225 B2 | 2/2010 | Chaouk et al. |
| 7,666,226 B2 | 2/2010 | Schaller |
| 7,666,227 B2 | 2/2010 | Schaller |
| 7,666,228 B2 | 2/2010 | Le Couedic et al. |
| 7,670,359 B2 | 3/2010 | Yundt |
| 7,670,374 B2 | 3/2010 | Schaller |
| 7,670,375 B2 | 3/2010 | Schaller |
| 7,670,377 B2 | 3/2010 | Zucherman et al. |
| 7,670,378 B2 | 3/2010 | Bloemer et al. |
| 7,670,379 B2 | 3/2010 | Cauthen |
| 7,670,380 B2 | 3/2010 | Cauthen, III |
| 7,670,636 B2 | 3/2010 | Berger et al. |
| 7,674,292 B2 | 3/2010 | Zubok et al. |
| 7,674,293 B2 | 3/2010 | Kuiper et al. |
| 7,674,294 B2 | 3/2010 | Karahalios et al. |
| 7,674,295 B2 | 3/2010 | Eckman |
| 7,674,296 B2 | 3/2010 | Rhoda et al. |
| 7,674,297 B2 | 3/2010 | Falahee |
| 7,674,852 B2 | 3/2010 | Muller et al. |

(56) References Cited

U.S. PATENT DOCUMENTS

| | | | |
|---|---|---|---|
| 7,678,112 B2 | 3/2010 | Rezach | |
| 7,678,116 B2 | 3/2010 | Truckai et al. | |
| 7,678,136 B2 | 3/2010 | Doubler et al. | |
| 7,678,137 B2 | 3/2010 | Butler et al. | |
| 7,678,148 B2 | 3/2010 | Peterman | |
| 7,678,149 B2 | 3/2010 | Bianchi et al. | |
| 7,682,376 B2 | 3/2010 | Trieu | |
| 7,682,392 B2 | 3/2010 | Serhan et al. | |
| 7,682,393 B2 | 3/2010 | Trieu et al. | |
| 7,682,394 B2 | 3/2010 | Recoules-Arche et al. | |
| 7,682,395 B2 | 3/2010 | Casey | |
| 7,682,396 B2 | 3/2010 | Beaurain et al. | |
| 7,682,400 B2 | 3/2010 | Zwirkoski | |
| 7,682,540 B2 | 3/2010 | Boyan et al. | |
| 7,686,805 B2 | 3/2010 | Michelson | |
| 7,686,832 B2 | 3/2010 | Jackson | |
| 7,687,098 B1 | 3/2010 | Chi | |
| 7,691,105 B2 | 4/2010 | Attawia et al. | |
| 7,691,129 B2 | 4/2010 | Felix | |
| 7,691,145 B2 | 4/2010 | Reiley et al. | |
| 7,691,147 B2 | 4/2010 | Gutlin et al. | |
| 7,691,148 B2 | 4/2010 | Michelson | |
| 7,695,500 B2 | 4/2010 | Markworth | |
| 7,695,513 B2 | 4/2010 | Zucherman et al. | |
| 7,695,514 B2 | 4/2010 | Kwak | |
| 7,695,516 B2 | 4/2010 | Zeegers | |
| 7,695,517 B2 | 4/2010 | Benzel et al. | |
| 7,695,518 B2 | 4/2010 | Gau | |
| 7,699,878 B2 | 4/2010 | Pavlov et al. | |
| 7,699,893 B2 | 4/2010 | Donnelly et al. | |
| 7,704,271 B2 | 4/2010 | Abdou | |
| 7,704,279 B2 | 4/2010 | Moskowitz et al. | |
| 7,704,280 B2 | 4/2010 | Lechmann et al. | |
| 7,704,281 B2 | 4/2010 | Pasquet et al. | |
| 7,704,529 B2 | 4/2010 | Riman et al. | |
| 7,708,760 B2 | 5/2010 | Parsons | |
| 7,708,765 B2 | 5/2010 | Carl et al. | |
| 7,708,776 B1 | 5/2010 | Blain et al. | |
| 7,708,777 B2 | 5/2010 | O'Neil et al. | |
| 7,708,778 B2 | 5/2010 | Gordon et al. | |
| 7,708,779 B2 | 5/2010 | Edie et al. | |
| 7,708,780 B2 | 5/2010 | Zubok et al. | |
| 7,713,289 B2 | 5/2010 | Matthys | |
| 7,713,302 B2 | 5/2010 | Ralph et al. | |
| 7,713,303 B2 | 5/2010 | Trieu et al. | |
| 7,713,304 B2 | 5/2010 | Ankney et al. | |
| 7,713,542 B2 | 5/2010 | Xu et al. | |
| 7,717,939 B2 | 5/2010 | Ludwig et al. | |
| 7,717,944 B2 | 5/2010 | Foley et al. | |
| 7,717,959 B2 | 5/2010 | William et al. | |
| 7,717,960 B2 | 5/2010 | Schneier | |
| 7,717,961 B2 | 5/2010 | Lambrecht et al. | |
| 7,722,610 B2 | 5/2010 | Viola et al. | |
| 7,722,611 B2 | 5/2010 | Cavallazzi et al. | |
| 7,722,620 B2 | 5/2010 | Truckai et al. | |
| 7,722,645 B2 | 5/2010 | Bryan | |
| 7,722,646 B2 | 5/2010 | Ralph et al. | |
| 7,722,647 B1 | 5/2010 | Wang et al. | |
| 7,722,651 B2 | 5/2010 | Kwak et al. | |
| 7,722,672 B2 | 5/2010 | Stone | |
| 7,722,673 B2 | 5/2010 | Keller | |
| 7,722,674 B1 | 5/2010 | Grotz | |
| 7,722,675 B2 | 5/2010 | Ralkph et al. | |
| 7,723,395 B2 | 5/2010 | Ringeisen et al. | |
| 7,726,002 B2 | 6/2010 | Shimp et al. | |
| 7,726,319 B1 | 6/2010 | Boyce | |
| 7,727,241 B2 | 6/2010 | Gorensek et al. | |
| 7,727,279 B2 | 6/2010 | Zipnick et al. | |
| 7,727,280 B2 | 6/2010 | McLuen | |
| 7,731,734 B2 | 6/2010 | Clement et al. | |
| 7,731,751 B2 | 6/2010 | Butler et al. | |
| 7,731,752 B2 | 6/2010 | Edie et al. | |
| 7,731,753 B2 | 6/2010 | Reo et al. | |
| 7,731,756 B2 | 6/2010 | Maspero et al. | |
| 7,732,573 B2 | 6/2010 | Tanaka et al. | |
| 7,736,369 B2 | 6/2010 | Arnin et al. | |
| 7,862,616 B2 | 1/2011 | Lechmann et al. | |
| 2001/0021851 A1 | 9/2001 | Eberlein et al. | |
| 2002/0128654 A1 | 9/2002 | Steger et al. | |
| 2003/0114931 A1 | 6/2003 | Lee et al. | |
| 2003/0130737 A1 | 7/2003 | McGahan et al. | |
| 2003/0139813 A1 | 7/2003 | Messerli et al. | |
| 2003/0149438 A1 | 8/2003 | Nichols et al. | |
| 2003/0195520 A1 | 10/2003 | Boyd et al. | |
| 2004/0002758 A1 | 1/2004 | Landry et al. | |
| 2004/0117020 A1 | 6/2004 | Frey et al. | |
| 2004/0127990 A1* | 7/2004 | Bartish et al. | 623/17.11 |
| 2004/0127994 A1 | 7/2004 | Kast et al. | |
| 2004/0267277 A1 | 12/2004 | Zannis et al. | |
| 2005/0021042 A1 | 1/2005 | Marnay et al. | |
| 2005/0027360 A1 | 2/2005 | Webb et al. | |
| 2005/0101960 A1* | 5/2005 | Fiere et al. | 606/72 |
| 2005/0113842 A1 | 5/2005 | Bertagnoli et al. | |
| 2005/0149188 A1 | 7/2005 | Cook et al. | |
| 2005/0165408 A1 | 7/2005 | Puno et al. | |
| 2005/0182416 A1 | 8/2005 | Lim et al. | |
| 2005/0283248 A1 | 12/2005 | Gordon et al. | |
| 2005/0288788 A1 | 12/2005 | Dougherty-Shah | |
| 2006/0030856 A1 | 2/2006 | Drewry et al. | |
| 2006/0030857 A1 | 2/2006 | de Villiers et al. | |
| 2006/0030862 A1 | 2/2006 | De Villiers et al. | |
| 2006/0052793 A1 | 3/2006 | Heinz | |
| 2006/0064107 A1 | 3/2006 | Bertagnoli et al. | |
| 2006/0149284 A1 | 7/2006 | McCormack et al. | |
| 2006/0167461 A1 | 7/2006 | Hawkins et al. | |
| 2006/0195190 A1 | 8/2006 | Lechmann et al. | |
| 2006/0235423 A1 | 10/2006 | Cantu | |
| 2006/0241641 A1 | 10/2006 | Albans et al. | |
| 2006/0241643 A1 | 10/2006 | Lim et al. | |
| 2007/0016220 A1 | 1/2007 | Michelson | |
| 2007/0016221 A1 | 1/2007 | Beyersdorff et al. | |
| 2007/0027544 A1* | 2/2007 | McCord et al. | 623/17.11 |
| 2007/0073298 A1 | 3/2007 | Beutter et al. | |
| 2007/0100452 A1 | 5/2007 | Prosser | |
| 2007/0123901 A1 | 5/2007 | Foley et al. | |
| 2007/0123903 A1 | 5/2007 | Raymond et al. | |
| 2007/0123904 A1 | 5/2007 | Stad et al. | |
| 2007/0191857 A1 | 8/2007 | Allard et al. | |
| 2007/0198025 A1 | 8/2007 | Trieu et al. | |
| 2007/0219635 A1 | 9/2007 | Mathieu et al. | |
| 2007/0233143 A1 | 10/2007 | Josse et al. | |
| 2007/0260315 A1 | 11/2007 | Foley et al. | |
| 2007/0270873 A1 | 11/2007 | Flickinger et al. | |
| 2008/0015695 A1 | 1/2008 | Eckman | |
| 2008/0021555 A1 | 1/2008 | White et al. | |
| 2008/0051890 A1 | 2/2008 | Waugh et al. | |
| 2008/0065219 A1 | 3/2008 | Dye | |
| 2008/0077153 A1 | 3/2008 | Pernsteiner et al. | |
| 2008/0077247 A1 | 3/2008 | Murillo et al. | |
| 2008/0082173 A1 | 4/2008 | Delurio et al. | |
| 2008/0114367 A1 | 5/2008 | Meyer | |
| 2008/0161817 A1 | 7/2008 | Parsons et al. | |
| 2008/0177275 A1 | 7/2008 | Wing et al. | |
| 2008/0221694 A1* | 9/2008 | Warnick et al. | 623/17.16 |
| 2008/0249624 A1 | 10/2008 | Josimovic-Alasevic et al. | |
| 2008/0249625 A1 | 10/2008 | Waugh et al. | |
| 2010/0137919 A1 | 6/2010 | Wolter | |
| 2010/0217393 A1 | 8/2010 | Theofilos | |
| 2010/0305704 A1 | 12/2010 | Messerli et al. | |
| 2010/0312346 A1 | 12/2010 | Kueenzi et al. | |
| 2010/0324683 A1 | 12/2010 | Reichen et al. | |
| 2011/0040382 A1 | 2/2011 | Muhanna | |
| 2011/0106260 A1 | 5/2011 | Laurence et al. | |

FOREIGN PATENT DOCUMENTS

| | | |
|---|---|---|
| WO | WO 99/38461 | 8/1999 |
| WO | WO 04/000177 | 12/2003 |
| WO | WO 2006/042335 | 4/2006 |

* cited by examiner

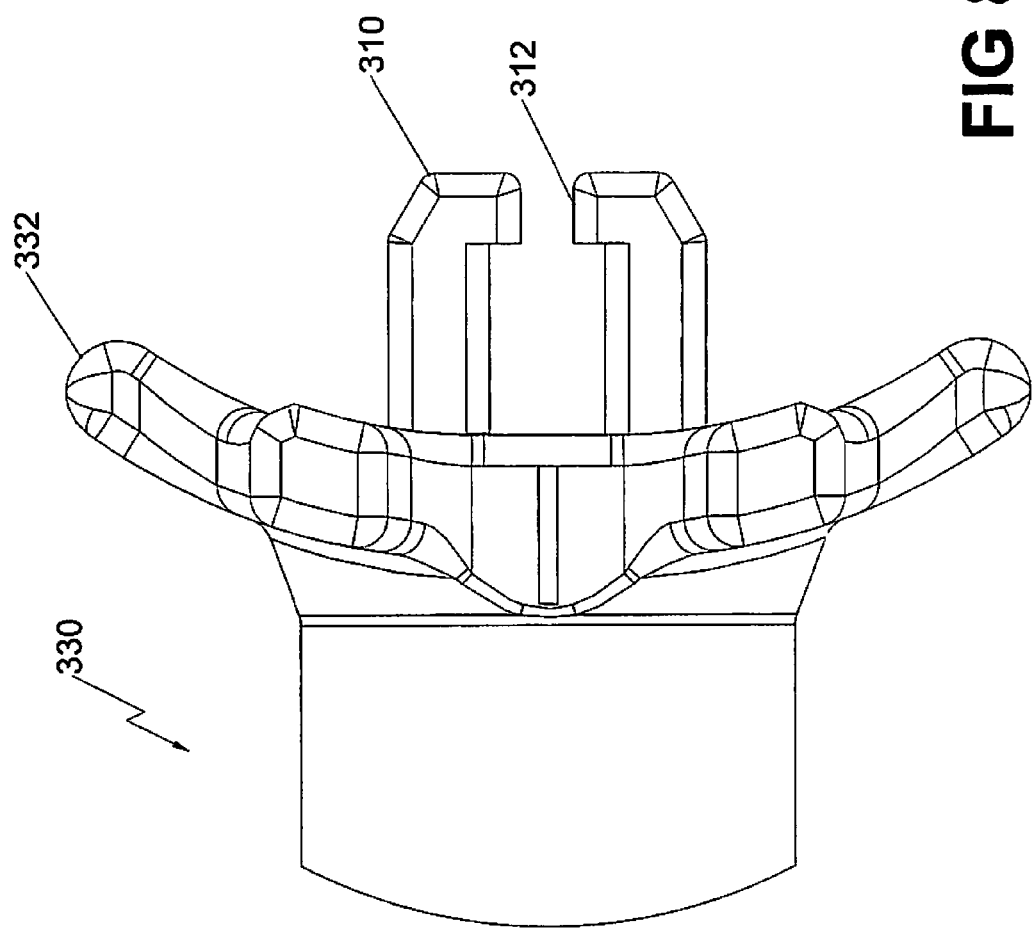

INTERBODY SPACER

CROSS-REFERENCE TO RELATED APPLICATION

This application claims priority to, and the benefit of, U.S. Provisional Patent Application No. 61/430,558, filed on Jan. 7, 2011, the entire contents of which are hereby incorporated by reference herein.

BACKGROUND

1. Technical Field

The present disclosure relates to an apparatus for treating spinal conditions, and more particularly, to an intervertebral implant and a method of use therefor.

2. Background of Related Art

The human spinal column is a highly complex structure. It includes twenty-four discrete bones, known as vertebrae, coupled sequentially to one another to house and protect critical elements of the nervous system. The cervical portion of the spine, which comprises the neck of the spine up to the base of the skull, includes the first seven vertebrae.

For many reasons, such as aging and trauma, the intervertebral discs can begin to deteriorate and weaken, potentially resulting in chronic pain or degenerative disc disease. Ultimately, the disc may deteriorate or weaken to the point of tearing and herniation, in which the inner portions of the disc protrude through the tear. A herniated disc may press against, or pinch, the spinal nerves, thereby causing radiating pain, numbness, tingling, and/or diminished strength or range of motion.

Many treatments are available to remedy these conditions, including surgical procedures in which one or more damaged intervertebral discs are removed and replaced with a prosthetic. After a partial or complete discectomy, the normally occupied space between adjacent vertebral bodies is subject to collapse and/or misalignment due to the absence of all or part of the intervertebral disc. In such situations, the physician may insert one or more prosthetic spacers between the affected vertebrae to maintain normal disc spacing and/or the normal amount of lordosis in the affected region.

Typically, a prosthetic implant is inserted between the adjacent vertebrae and may include pathways that permit bone growth between the adjacent vertebrae until they are fused together. However, there exists a possibility that conventional prosthetic implants may be dislodged and moved from their desired implantation location due to movement by the patient before sufficient bone growth has occurred.

Therefore, a need exists for a spinal implant that resists dislocation from the implantation site, while allowing for bone growth between the adjacent vertebrae.

SUMMARY

In accordance with an embodiment of the present disclosure, there is provided an interbody spacer including a connecting portion and a pair of leg portions extending from the connecting portion. The connecting portion and the pair of leg portions define top and bottom surfaces configured and adapted to engage first and second vertebral bodies, respectively, and inner and outer sidewalls extending between the top and bottom surfaces. The top and bottom surfaces of the leg portions include first projections defining a first angle with the respective top and bottom surfaces of the leg portions. The top and bottom surfaces of the connecting portion include second projections defining a second angle with the respective top and bottom surfaces of the connecting portion. The first and second angles are different.

In an embodiment, the first angle may be less than the second angle. The top and bottom surfaces may further include third projections disposed between the first and second projections. The third projections may each have a first side defining an angle with respective top and bottom surface that is substantially identical to the first angle and a second side defining an angle with respective top and bottom surface that is substantially identical to the second angle. The first projections may be uniformly spaced apart. Similarly, the second projections may also be uniformly spaced apart. In addition, the first and second projections may be symmetrically arranged on the top and bottom surfaces. The interbody spacer may have a substantially U-shaped configuration.

In another embodiment, the outer sidewall may define a pair of apertures in communication with each other. The outer sidewall may include a dividing wall interposed between the pair of apertures. The pair of leg portions may define a gap therebetween. The leg portions may each define at least one bore extending between the inner sidewall and the outer sidewall. The bore may be in communication with the gap. In addition, the pair of apertures may be in communication with the gap.

In accordance with another embodiment of the present disclosure, there is provided an interbody spacer system including an interbody spacer having a substantially U-shaped configuration and a surgical instrument. The interbody spacer includes a connecting portion and a pair of leg portions extending from the connecting portion. The connecting portion and the pair of leg portions define top and bottom surfaces configured and adapted to engage first and second vertebral bodies, respectively, and inner and outer sidewalls extending between the top and bottom surfaces. The outer sidewall defines a pair of apertures. The top and bottom surfaces of the leg portions include first projections defining a first angle with the respective top and bottom surfaces of the leg portions. The top and bottom surfaces of the connecting portion include second projections defining a second angle with the respective top and bottom surfaces of the connecting portion. The first angle is less than the second angle. The surgical instrument includes an elongate body and a grasping assembly operatively coupled to the elongate body. The grasping assembly includes a pair of graspers configured and dimensioned to be received in the pair of apertures defined in the outer sidewall of the interbody spacer. The graspers are movable between an open, spaced apart position and a gripping position in which the pair of graspers are moved toward each other.

In embodiment, the interbody spacer may include at least one radiopaque marker. The outer sidewall may have an arcuate profile. The grasping assembly may include a contacting support configured and adapted to engage and accommodate the contour of the outer sidewall. The outer sidewall may include a dividing wall interposed between the pair of apertures. The graspers may securely engage the dividing wall when the graspers are in the gripping position.

In yet another embodiment, the outer sidewall may include a portion having third projections configured and adapted to provide gripping texture to the surgical instrument coupled with the interbody spacer.

In accordance with another aspect of the present disclosure, there is provided a method of securing adjacent vertebral bodies. The method includes providing an interbody spacer system including an interbody spacer and a surgical instrument, distracting the adjacent first and second vertebral bodies and inserting the interbody spacer between the first and second vertebral bodies. In particular, the interbody spacer includes a connecting portion and a pair of leg portions extending from the connecting portion. The connecting portion and the pair of leg portions define top and bottom surfaces configured and adapted to engage first and second vertebral bodies, respectively. The top and bottom surfaces of the leg portions include first projections defining a first angle with the respective top and bottom surfaces of the leg portions. The top and bottom surfaces of the connecting portion include second projections defining a second angle with the respective top and bottom surfaces of the connecting portion. The surgical instrument includes an elongate body and a grasping assembly operatively coupled to the elongate body. The grasping assembly includes a pair of graspers configured to securely couple the interbody spacer to the surgical instrument. The graspers are movable between an open, spaced apart position and a gripping position in which the pair of graspers are moved toward each other.

In an embodiment, the method may further include identifying the correct operative level and making an incision in the patient. Moreover, the method may further include removing vertebral tissue. In another embodiment, inserting the interbody spacer between the first and second vertebral bodies may include coupling the interbody spacer with the surgical instrument. Coupling the interbody spacer with the surgical instrument may include positioning the graspers into a pair of apertures defined in the interbody spacer and moving the pair of graspers to the gripping position. In yet another embodiment, the method may further include visualizing interbody spacer in vivo. The method may also include placing bone graft through the apertures.

BRIEF DESCRIPTION OF THE DRAWINGS

Various embodiments of the present disclosure are described hereinbelow with reference to the drawings, wherein:

FIG. 8 is a top, plan view of the area of detail indicated in FIG. 6.

DETAILED DESCRIPTION OF EMBODIMENTS

Figure 1:
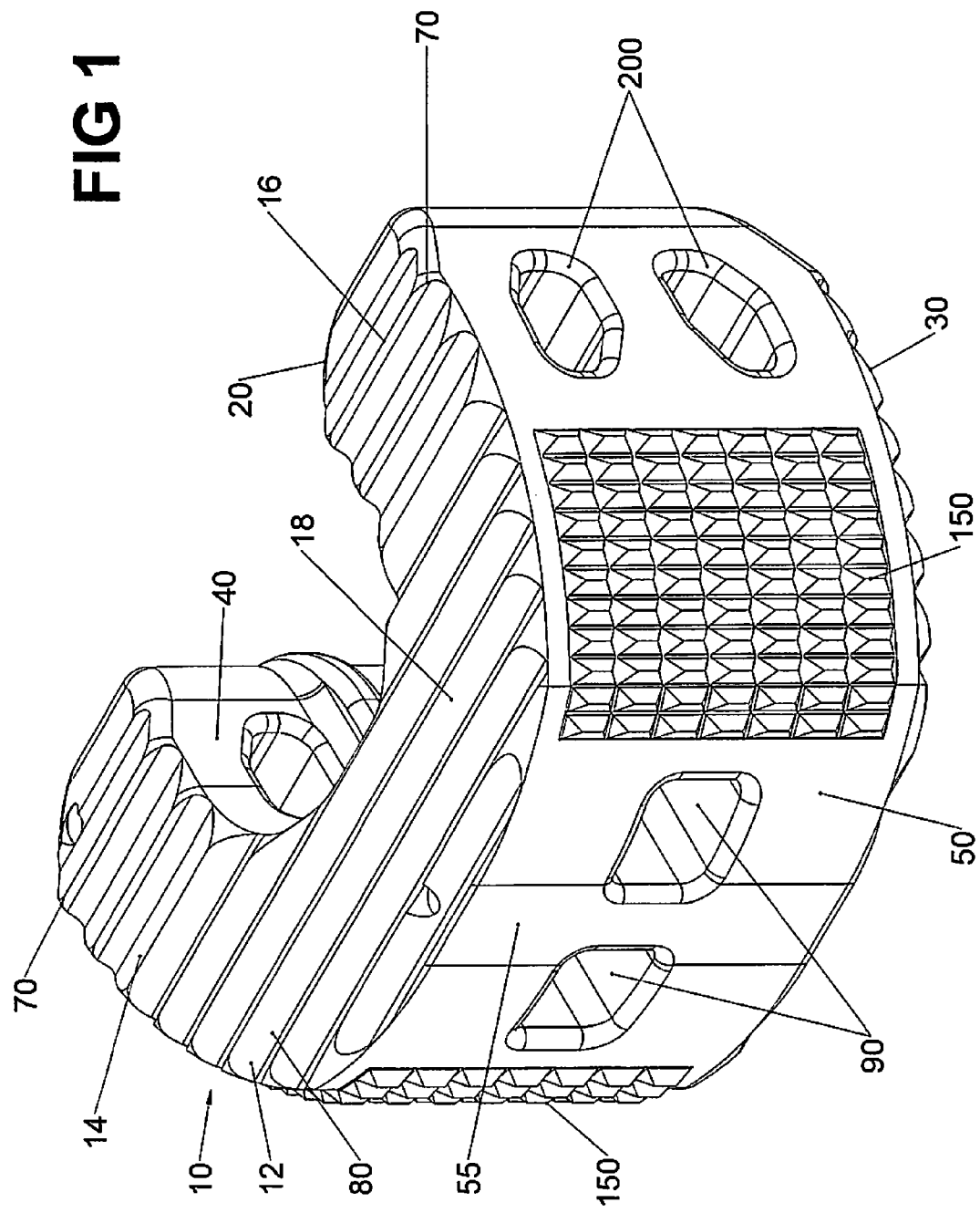
FIG. 1 is a perspective view of an interbody spacer device in accordance with an embodiment of the present disclosure.

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In addition, the term "cephalad" is used in this application to indicate a direction toward a patient's head, while the term "caudad" indicates a direction toward the patient's feet. Further still, for the purposes of this application, the term "medial" indicates a direction toward the middle of the body of the patient, while the term "lateral" indicates a direction toward a side of the body of the patient, i.e., away from the middle of the body of the patient. The term "posterior" indicates a direction toward the patient's back, while the term "anterior" indicates a direction toward the patient's front. In the following description, well-known functions or constructions are not described in detail to avoid obscuring the present disclosure in unnecessary detail.

With reference to FIG. 1, an embodiment of the present disclosure is shown generally as an interbody spacer device 10 configured and adapted to be positionable between adjacent vertebral bodies to support the vertebral bodies and to promote spinal fusion. Interbody spacer device 10 inhibits the collapse of the space between adjacent vertebrae, typically after a full or partial discectomy. Interbody spacer device 10 is positioned between adjacent vertebrae to maintain normal disc spacing and/or the normal amount of lordosis in the affected region of the discectomy.

Interbody spacer device 10 may be made of titanium, titanium alloy, stainless steel, allograft bone, autologous bone graft, polyetheretherketone (PEEK), polysulfone (RADEL), polyetherimide (ULTEM), cobalt chrome, polymeric materials, a combination thereof, or any other suitable biocompatible material. In particular, interbody spacer device 10 may be formed of bone, or an artificial material other than bone, which may be harder or stronger than bone, such as, e.g., ceramic materials. Interbody spacer device 10 may include a bone growth promoting material such as, e.g., bone morphogenic protein and hydroxyapatite. Spacer device 10 may be fabricated from multiple components. Alternatively, interbody spacer device 10 may be formed monolithically as a single construct.

Figure 2:
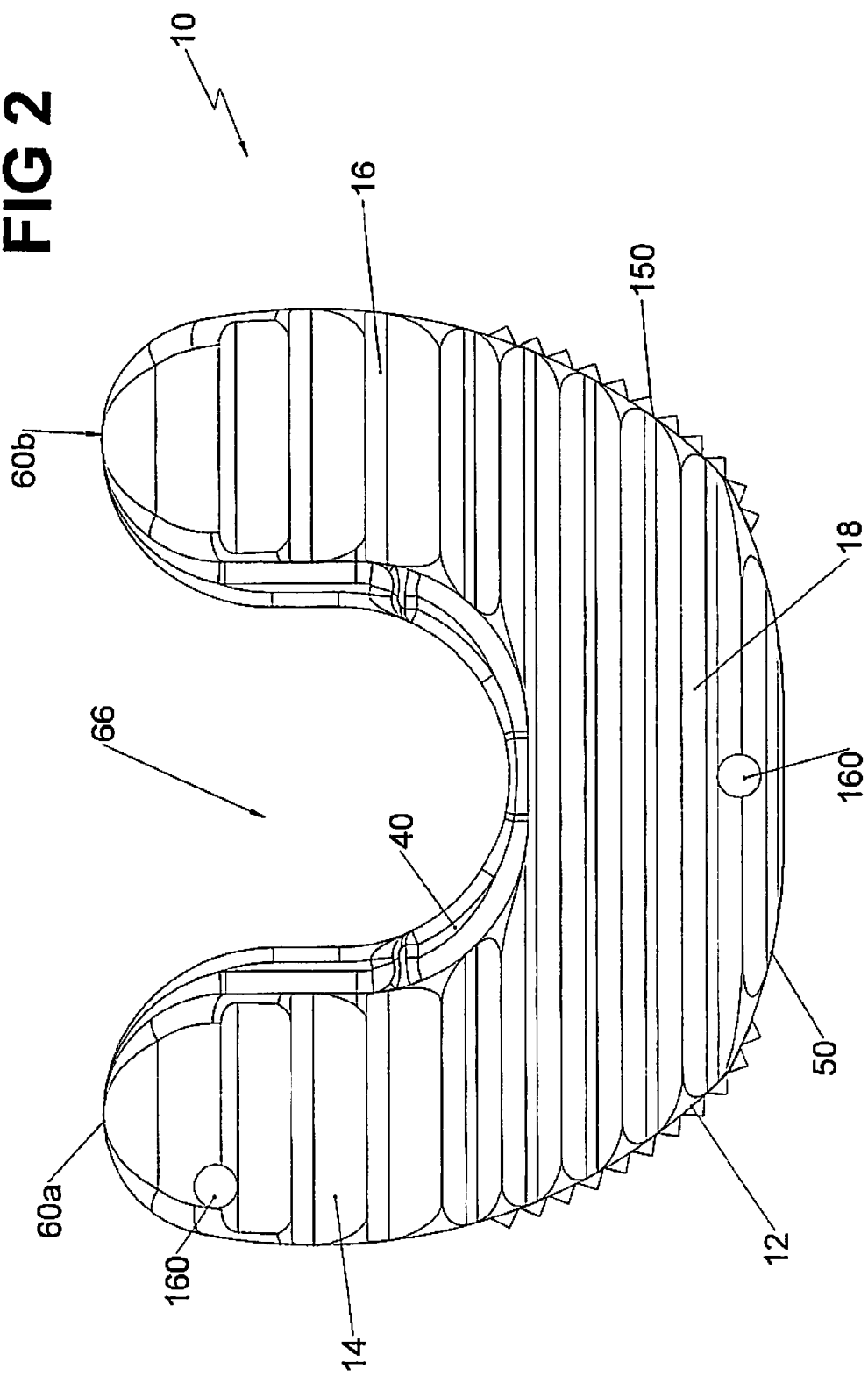
FIG. 2 is a top, plan view of the interbody spacer device of FIG. 1.

With reference now to FIGS. 1 and 2, interbody spacer device 10 includes a substantially semi-circular shaped body portion 12 defining a substantially U-shaped profile. Body portion 12 includes a connecting portion 18 and a pair of leg portions 14, 16 extending distally from connecting portion 18. Body portion 12 includes substantially parallel top and bottom surfaces 20, 30 configured to engage vertebral bodies. In addition, body portion 12 includes inner and outer sidewalls 40, 50 extending between top and bottom surfaces 20, 30. In particular, inner and outer sidewalls 40, 50 are substantially orthogonal to top and bottom surfaces 20, 30.

With continued reference to FIGS. 1 and 2, body portion 12 defines a recess 66 between leg portions 14, 16 for containment of additional bone graft material to facilitate fusion. Leg portions 14, 16 include respective distal end portions 60a, 60b. End portions 60a, 60b are angled or curved in a plurality of planes to provide blunt or atraumatic tip characteristics to facilitate insertion of interbody spacer device 10 between vertebrae. In particular, distal end portions 60a, 60b each have a radius of curvature of about 0.082 inch. The radius of curvature may generally be within the range of about 0.060 inch to about 0.110 inch.

Figure 4:
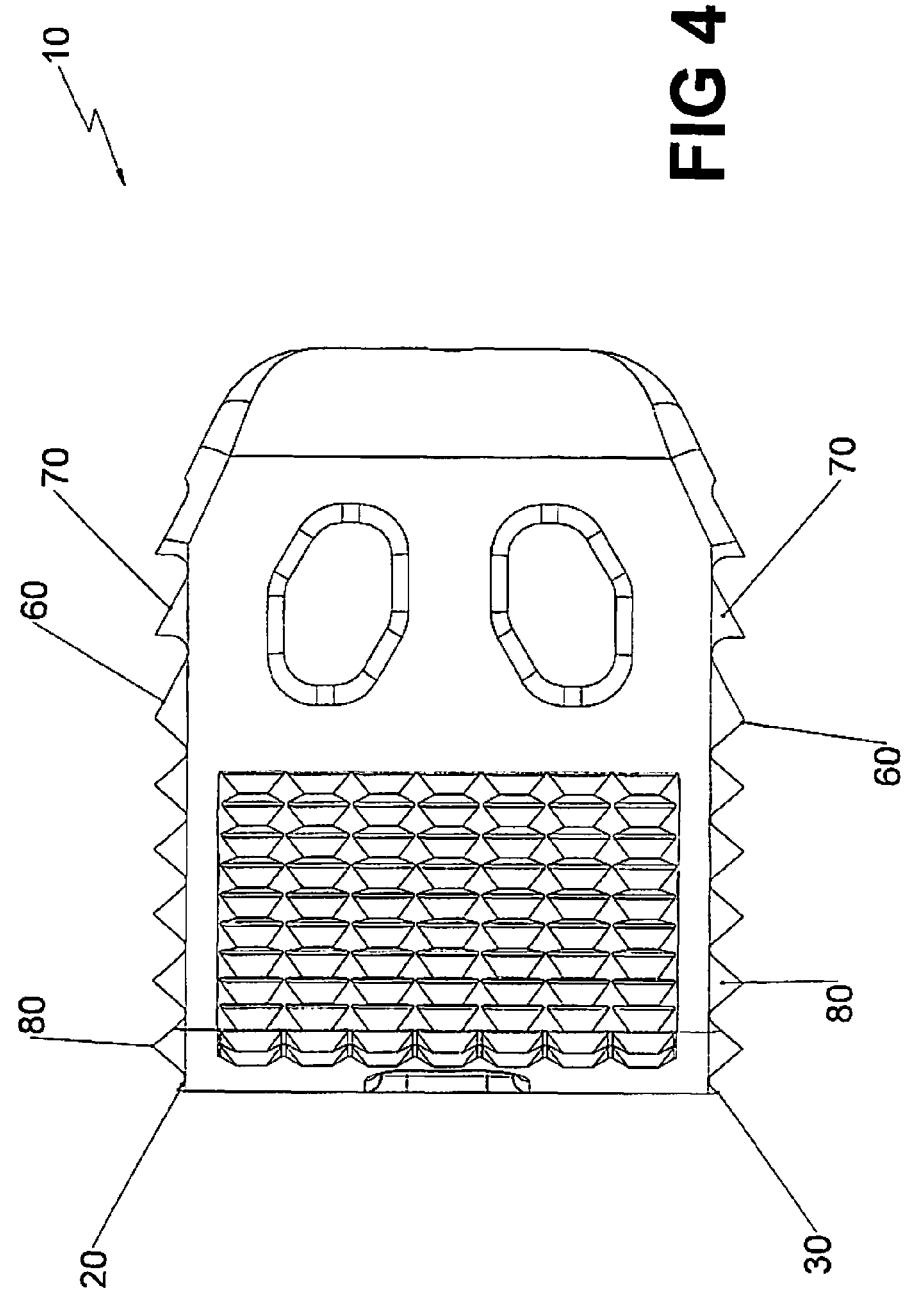
FIG. 4 is a side view of the interbody spacer device of FIG. 1.

With particular reference now to FIGS. 2 and 4, top and bottom surfaces 20, 30 are configured and adapted to engage, for example, endplates of superior and inferior vertebral bodies, respectively. Each of top and bottom surfaces 20, 30 define ridges or projections 60, 70, 80 configured and adapted to enhance grip against respective vertebral bodies and stability against fore and aft, oblique or side to side movement of interbody spacer device 10 within the disc space.

Figure 7:
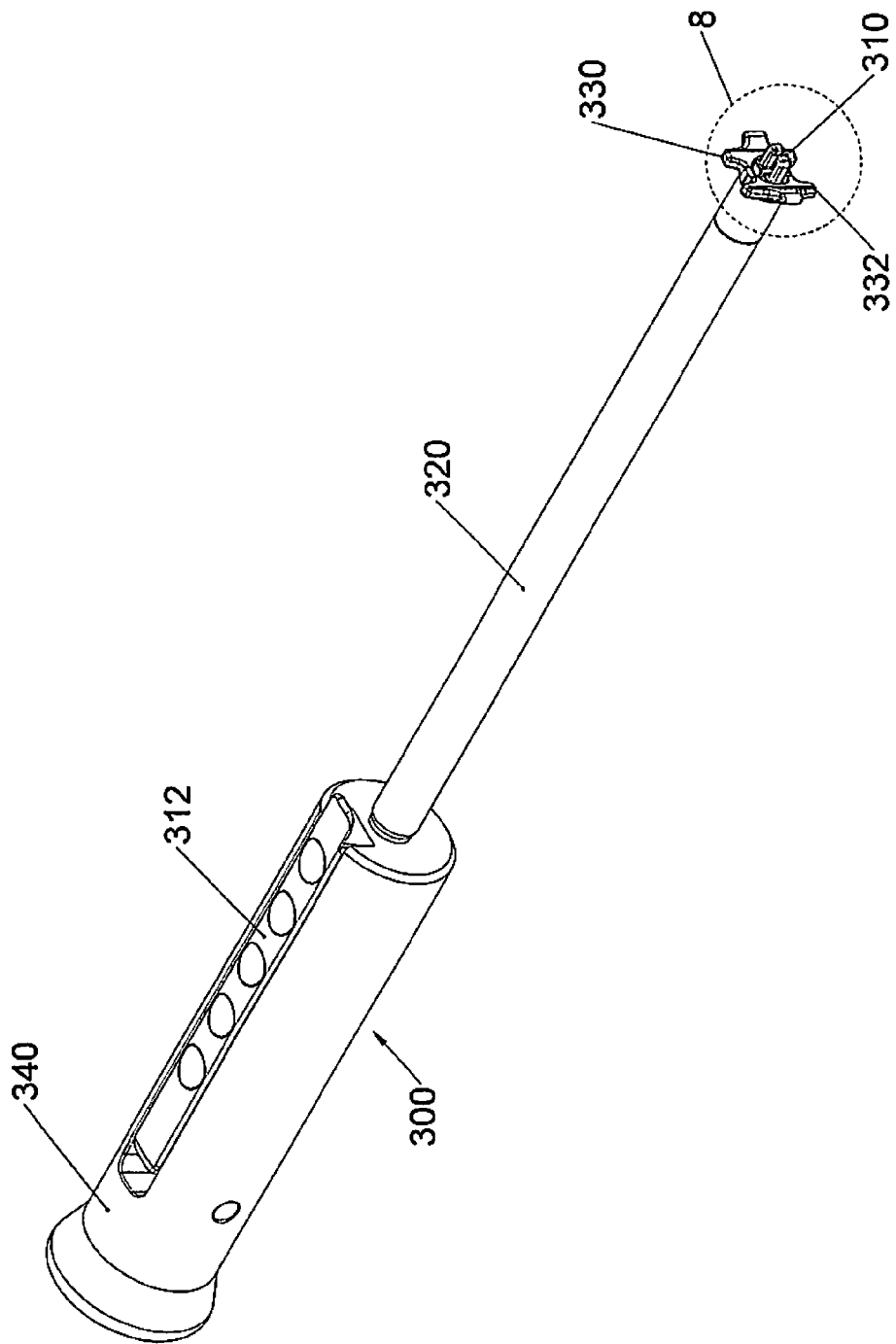
FIG. 7 is a perspective view of a surgical device for use with the interbody spacer devices of FIGS. 1 and 6.

With continued reference to FIG. 4, projections 70 are disposed on top and bottom surfaces 20, 30 of leg portions 14, 16. Projections 70 enable manipulation of interbody spacer device 10 into the correct orientation and placement through manipulation with a surgical instrument 300 (FIG. 7). Projections 70 are substantially identical to each other. Projections 70 have a height of about 0.020 inch and are spaced about 0.050 inches apart from each other. Projections 70 on top and bottom surfaces 20, 30 are symmetric. One side of each projection 70 defines an angle of about 28 degrees with respective top and bottom surfaces 20, 30 and another side of projection 70 defines an arcuate portion. Additionally, projections 70 define a peak-to-peak angle of about 62 degrees.

Projections 80 are disposed on top and bottom surfaces 20, 30 of body portion 12. Projections 80 are substantially identical to each other. In particular, projections 80 have a height of about 0.020 inches and are spaced about 0.040 inches apart from each other. Similar to projections 70, projections 80 on top and bottom surfaces 20, 30 are symmetric. Projections 70 each define an angle of about 48 degrees with the respective top and bottom surfaces 20, 30.

Projections 60 are positioned between projections 70, 80. Projections 60 are substantially identical to each other and are symmetrical on the respective top and bottom surfaces 20, 30. In particular, one side of projection 60 defines an angle that is substantially identical to that of projections 70 and another side defines an angle that is substantially identical to that of projections 80.

Projections 60, 70, 80 of different geometric patterns facilitate insertion of interbody spacer device 10 into the disc space, while minimizing the ability of interbody spacer device 10 to retropulse out of the disc space or become dislodged and cause damage to the surrounding anatomy.

Figure 3:
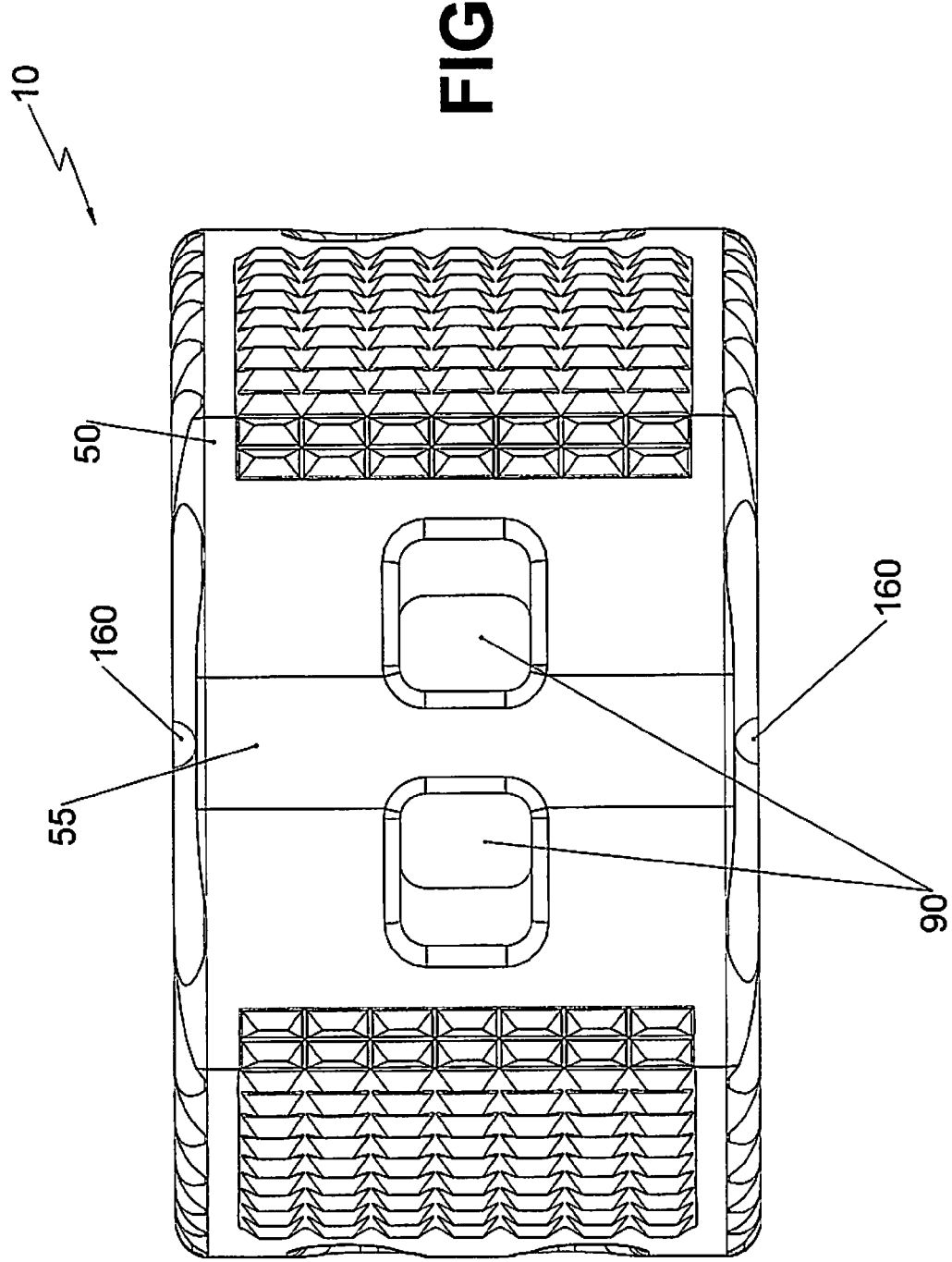
FIG. 3 is a front view of the interbody spacer device of FIG. 1.
Figure 5:
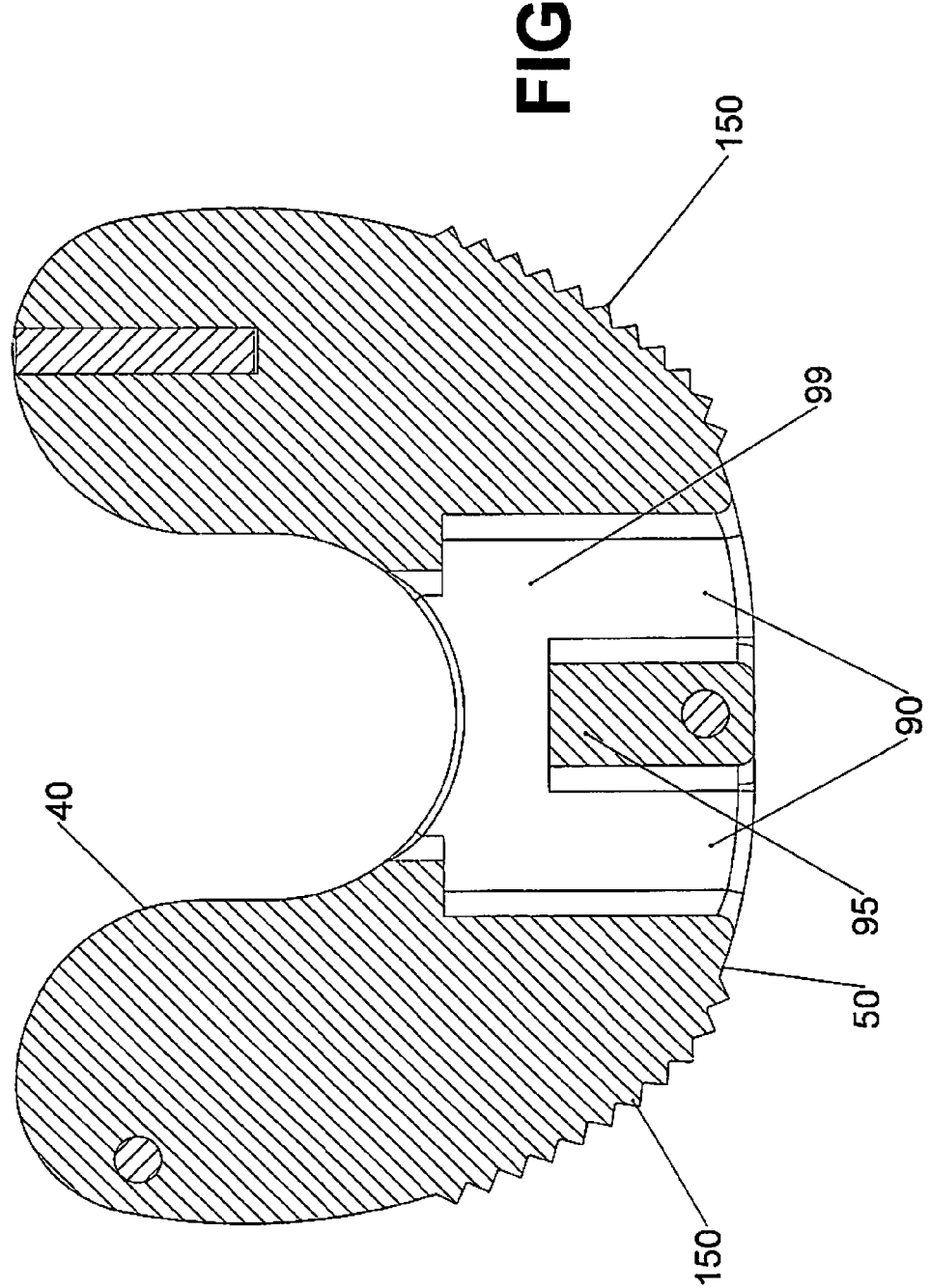
FIG. 5 is a cross-sectional view of the interbody spacer device of FIG. 1.

With reference now to FIGS. 1, 3 and 5, outer sidewall 50 has an arcuate profile and has a radius of curvature of about 0.353 inch. The radius of curvature may generally be within the range of about 0.30 inch to about 0.40 inch. Outer sidewall 50 defines a pair of apertures 90 at a proximal-most portion 55 of outer sidewall 50. Apertures 90 are in communication with each other and form a recess 99 (FIG. 5). In addition, outer sidewall 50 includes a dividing wall 95 (FIG. 5) interposed between apertures 90 within recess 99. Apertures 90 are configured and dimensioned to receive respective graspers 310 (FIG. 8) of surgical instrument 300 (FIG. 7) configured and adapted to grasp interbody spacer device 10 for insertion and removal of interbody spacer device 10 into and from the disc space, as well as manipulation of interbody spacer device 10 for positioning within the disk space. In particular, gaspers 310 grasp dividing wall 95 of interbody spacer device 10.

With continued reference to FIG. 5, outer sidewall 50 includes portions having projections 150 configured to provide surface texture to facilitate manipulation of various surgical instruments thereon. For example, contact support 332 (FIG. 8) of surgical instrument 300 engages projections 150 to push or pivot interbody spacer device 10 into the correct orientation within the disc space. Projections 150 may have various heights, widths, lengths, patterns and shapes. Projections 150 are substantially identical to each other. Projections 150 have a height of about 0.010 inch and a width of about 0.021 inch. Moreover, projections 150 are spaced about 0.021 inches apart from each other. Each projection 150 defines an angle of about 45 degrees with respect to outer sidewall 50. Projections 150 are symmetrically disposed on outer sidewall 50 with respect to apertures 90. However, the number of projections 150, as well as location on interbody spacer device 10 may be tailored to the particular surgical instrument being used.

With reference back to FIGS. 1 and 2, outer sidewall 50 may further define recesses 200 on respective leg portions 14, 16. Recesses 200 extend from outer sidewall 50 to inner sidewall 40. In this manner, recesses 200 enable visualization of the bone raft material and facilitate the reception of bone graft material therethrough. Inner sidewall 40 defines recess 66 having an arcuate profile. Inner sidewall 40 has a radius of curvature of about 0.114 inch. The radius of curvature may generally be within the range of about 0.1 inch to about 0.2 inch.

With particular reference to FIGS. 2 and 3, interbody spacer device 10 includes bores 160 configured and dimensioned to accommodate radiopaque markers therein to aid visualization of interbody spacer 10 in vivo. The markers in bores 160 ensure that interbody spacer device 10 has been placed correctly during the surgery though image guidance, such as fluoroscopy.

With reference now to FIG. 7, surgical instrument 300 is utilized to insert and remove interbody spacer device 10 into and from the disc space. Surgical instrument 300 includes a handle portion 340, an elongate body 320 extending distally from handle portion 340, and a grasper assembly 330 operatively coupled to handle portion 340. Handle portion 340 includes a slider 312 slidably disposed on handle portion 340 and operatively coupled to graspers 310 of grasper assembly 330. Translation of slider 312 moves graspers 310 between a spaced apart position to a gripping position in which graspers 310 are moved toward each other.

With reference now to FIG. 8, grasper assembly 330 includes a contact support 332 configured and dimensioned to engage at least a portion of outer sidewall 50 of interbody spacer device 10 and a pair of gaspers 310 that move between a spaced apart position and the gipping position. Contact support 332 is configured to accommodate the contour of the arcuate profile of outer sidewall 50. Each grasper 310 includes a finger 312 extending inward such that when graspers 310 are in the gripping position, fingers 312 are secured against dividing wall 95.

In use, the surgeon uses fluoroscopy or another imaging modality to identify the correct operative level and makes one or more incisions through the patient's skin using conventional instruments. The number and type of incisions made (e.g. transverse or vertical) is related to the procedure to be performed. Graspers 310 of surgical instrument 300 are placed in respective apertures 90 of interbody spacer device 10. The surgeon can actuate slider 312 to securely lock graspers 310 against dividing wall 95 of interbody spacer device 10. After coupling interbody spacer device 10 to surgical instrument 300, interbody spacer device 10 is placed into the prepared disc space so that outer sidewall 50 is in vertical alignment with the ephiphyseal ring on the vertebral bodies. This provides the maximum support for the vertebral bodies when under load, which helps to maintain the placement of spacer device 10 post-operatively. A mallet and slap hammer (not shown) may also be used to facilitate placement of interbody spacer device 10. If needed, the surgeon may place various types of bone graft into through aperture 90 prior to insertion in order to help facilitate the fusion process.

Figure 6:
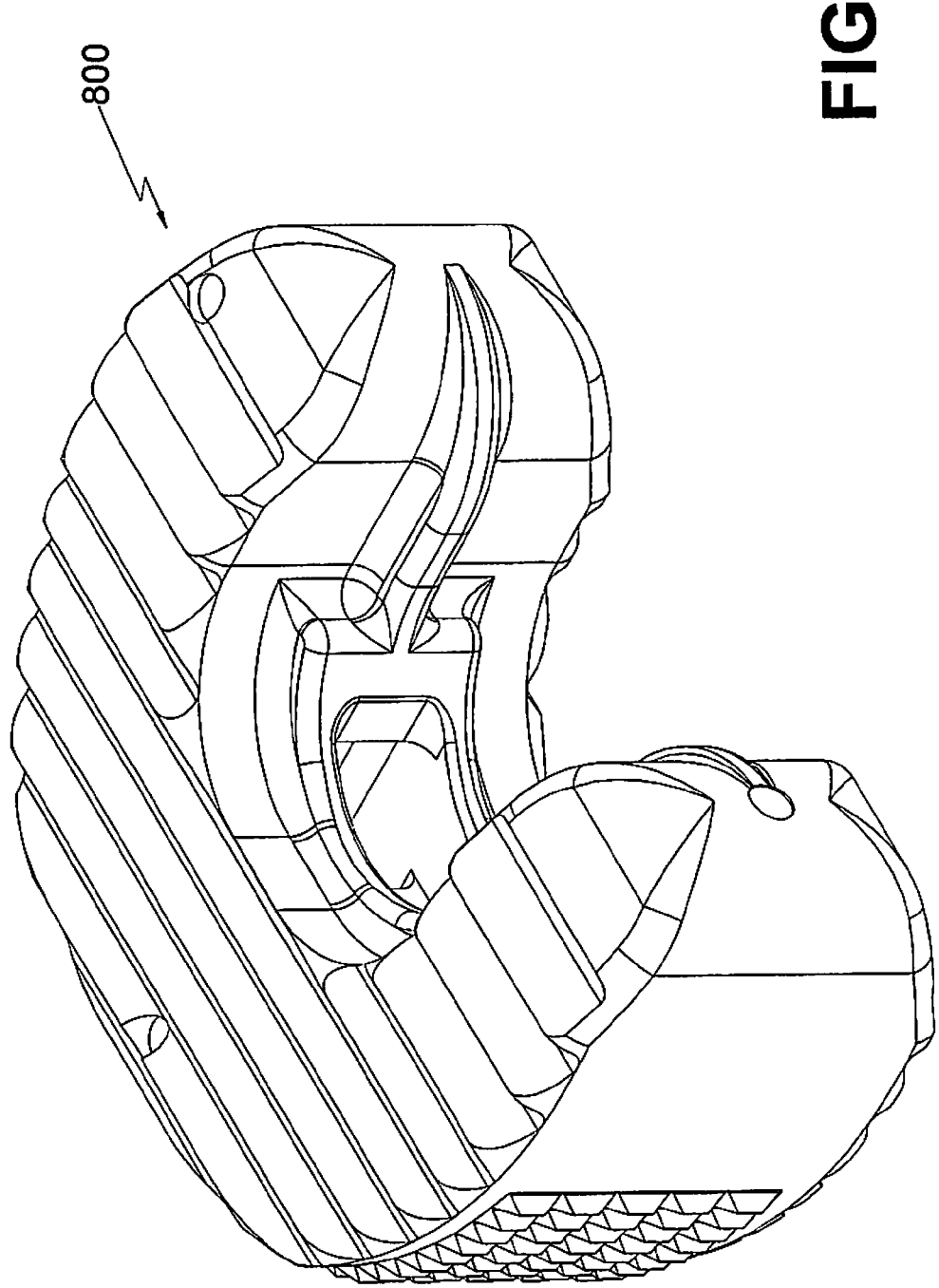
FIG. 6 is a perspective view of an interbody spacer device in accordance with another embodiment of the present disclosure.

It is further contemplated that an interbody spacer 800 may be tapered to facilitate insertion thereof into the intervertebral space and provide an amount of lordosis, as shown in FIG. 6. It is envisioned that interbody spacer device 10, 800 may be tailored to the particular surgical procedure being performed, whereby the length, width, and height of interbody spacer device 10, 800 may be modified. In addition, spacer device 10, 800 may be provided with bone graft along inner sidewall 40 to provide additional means of bone fusion. Bone graft can also be packed into place prior to placement of spacer device 10 or after placement by use of apertures 90.

Although the illustrative embodiments of the present disclosure have been described herein with reference to the accompanying drawings, the above description, disclosure, and figures should not be construed as limiting, but merely as exemplifications of particular embodiments. For example, outer sidewall 50 of interbody spacer device 10 may be placed in the disc space first such that the surgeon may access recess 66 to place bone graft therein. One skilled in the art will recognize that the disclosure is not limited to use in the lumbar region or spine surgery, and that the instrument and methods can be adapted for use with any suitable surgical device. Those skilled in the art will appreciate that the present disclosure may be implemented in a number of different applications and embodiments and is not specifically limited in its application to the particular embodiments depicted herein. It is to be understood, therefore, that the disclosure is not limited to those precise embodiments, and that various other changes and modifications may be effected therein by one skilled in the art without departing from the scope or spirit of the disclosure.

What is claimed is:

1. An interbody spacer comprising:
    a connecting portion;
    a pair of leg portions extending from the connecting portion, the connecting portion and the pair of leg portions defining top and bottom surfaces configured and adapted to engage first and second vertebral bodies, respectively, and inner and outer sidewalls extending between the top and bottom surfaces, wherein the top and bottom surfaces of the leg portions include first projections defining a first angle with the respective top and bottom surfaces of the leg portions, and the top and bottom surfaces of the connecting portion include second projections defining a second angle with the respective top and bottom surfaces of the connecting portion, the first and second angles being different, wherein the outer sidewall includes third projections configured to engage with a contact support of a surgical tool, the third projections located on an outer surface of the outer sidewall; and
    a pair of apertures located on a proximal portion of the connecting portion and extending therethrough, the pair of apertures separated by a dividing wall that defines a recess, the recess located on the connecting portion and laterally spaced from outer surfaces of the pair of legs, the pair of apertures dimensioned such that the dividing wall may be grasped by a surgical tool, wherein each aperture of the pair of apertures is adjacent to and in communication with the other aperture of the pair of apertures, and the inner and outer sidewalls have an arcuate profile.

2. The interbody spacer according to claim 1, wherein the first angle is less than the second angle.

3. The interbody spacer according to claim 1, wherein the top and bottom surfaces further include fourth projections disposed between the first and second projections, the fourth projections each having a first side defining an angle with respective top and bottom surfaces that is substantially identical to the first angle and a second side defining an angle with respective top and bottom surfaces that is substantially identical to the second angle.

4. The interbody spacer according to claim 1, wherein the first projections are uniformly spaced apart.

5. The interbody spacer according to claim 1, wherein the second projections are uniformly spaced apart.

6. The interbody spacer according to claim 1, wherein the first and second projections are symmetrically arranged on the top and bottom surfaces.

7. The interbody spacer according to claim 1, wherein the interbody spacer has a substantially U-shaped configuration.

8. The interbody spacer according to claim 1, wherein the pair of leg portions define a gap therebetween.

9. The interbody spacer according to claim 8, wherein the leg portions each define at least one bore extending between the inner sidewall and the outer sidewall.

10. The interbody spacer according to claim 9, wherein the at least one bore is in communication with the gap.

11. The interbody spacer according to claim 1, wherein the pair of apertures are in communication with the gap.

12. The interbody spacer according to claim 1, wherein the third projections are adjacent to at least one of the pair of apertures defined in the outer sidewall.

13. The interbody spacer according to claim 1, wherein each of the third projections defines an angle with respect to the outer sidewall.

14. The interbody spacer according to claim 1, wherein first and second fingers of a surgical tool are laterally spaced from outer edges of the leg portions with the first and second fingers positioned in the recess.

15. The interbody spacer according to claim 1, wherein one aperture of the pair of apertures is adjacent the other aperture of the pair of apertures.

16. The interbody spacer according to claim 1, wherein the recess is in communication with a space defined between the pair of legs.

17. An interbody spacer comprising:
    a connecting portion;
    first and second leg portions extending from the connecting portion;
    top and bottom surfaces defined by the first leg, the second leg, and the connecting portion, the top and bottom surfaces configured to engage first and second vertebral bodies;
    first projections disposed on top and bottom surfaces of the leg portions and defining a first angle with the respective top and bottom surfaces of the first and second leg portions;
    second projections located on the connecting portion and defining a second angle with the respective top and bottom surfaces of the connecting portion, the second angle being different from first angle;
    third projections positioned on outer surfaces of the first and second leg portions;
    first and second apertures located on the connecting portion and extending therethrough, the first aperture being adjacent to the second aperture, the first and second apertures being laterally spaced from the outer surfaces of the first and second leg portions;
    a space defined between first and second leg portions, the first and second apertures in communication with the space, the connecting portion, and each other; and
    a recess defined by the first aperture, the second aperture, and a dividing wall, the dividing wall separating the first aperture from the second aperture, the recess laterally spaced from outer surfaces of the first and second legs.

18. The interbody spacer of claim 17, wherein the recess is configured to receive first and second fingers of a surgical tool such that the first and second fingers are laterally spaced from the outer surfaces of the first and second leg portions.

* * * * *